United States Patent
Kagan (10) Patent No.: US 8,372,060 B2
(45) Date of Patent: Feb. 12, 2013

(54) CATHETER/FILAMENT STYLE DEVICE AND METHODS FOR TREATMENT OF WOUNDS BENEATH THE SURFACE OF THE SKIN

(75) Inventor: Jonathan Kagan, Hopkins, MN (US)

(73) Assignee: KCI Licensing, Inc., San Antonio, TX (US)

( * ) Notice: Subject to any disclaimer, the term of this patent is extended or adjusted under 35 U.S.C. 154(b) by 629 days.

(21) Appl. No.: 12/465,462

(22) Filed: May 13, 2009

(65) Prior Publication Data

US 2009/0287181 A1  Nov. 19, 2009

Related U.S. Application Data

(60) Provisional application No. 61/052,867, filed on May 13, 2008.

(51) Int. Cl.
*A61M 1/00* (2006.01)
(52) U.S. Cl. .................. 604/541; 604/540; 604/543
(58) Field of Classification Search .............. 604/543, 604/313–316
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |

(Continued)

FOREIGN PATENT DOCUMENTS

| | | |
|---|---|---|
| AU | 550575 A1 | 8/1982 |
| AU | 745271 | 4/1999 |

(Continued)

OTHER PUBLICATIONS

International Search Report and Written Opinion date mailed Sep. 18, 2009; PCT International Application No. PCT/US2009/043778.

(Continued)

*Primary Examiner* — Susan Su (57) ABSTRACT

A reduced pressure treatment system includes a filament delivery conduit having a distal end positioned at a subcutaneous tissue site of a patient and a proximal end positioned extracorporeal to the patient. A continuous filament is positioned in the filament delivery conduit such that one end of the continuous filament extends from the proximal end of the filament delivery conduit and another end of the continuous filament extends from the distal end of the filament delivery conduit. The continuous filament forms a filament mass adjacent the tissue site. A reduced pressure delivery conduit is adapted to fluidly communicate with a reduced pressure source and the filaments mass to deliver a reduced pressure to the tissue site through the filament mass.

24 Claims, 8 Drawing Sheets

U.S. PATENT DOCUMENTS

| | | | |
|---|---|---|---|
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,578,055 | A * | 3/1986 | Fischer .......................... 604/2 |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt et al. |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,061,274 | A * | 10/1991 | Kensey .......................... 606/213 |
| 5,086,170 | A | 2/1992 | Luheshi et al. |
| 5,090,408 | A * | 2/1992 | Spofford et al. ......... 128/207.14 |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,492 | A * | 10/1994 | Feibus .......................... 604/264 |
| 5,358,494 | A | 10/1994 | Svedman |
| 5,431,639 | A * | 7/1995 | Shaw .......................... 604/264 |
| 5,437,622 | A | 8/1995 | Carion |
| 5,437,651 | A | 8/1995 | Todd et al. |
| 5,478,308 | A * | 12/1995 | Cartmell et al. ................ 602/57 |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 5,885,237 | A * | 3/1999 | Kadash et al. .................. 602/48 |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,565,544 | B1 * | 5/2003 | Rainin .......................... 604/313 |
| 6,814,079 | B2 | 11/2004 | Heaton et al. |
| 7,182,758 | B2 * | 2/2007 | McCraw ...................... 604/541 |
| 7,318,840 | B2 * | 1/2008 | McKay ...................... 623/17.11 |
| 7,524,315 | B2 * | 4/2009 | Blott et al. ...................... 604/543 |
| 7,754,937 | B2 * | 7/2010 | Boehringer et al. ............ 602/53 |
| 2002/0026244 | A1 * | 2/2002 | Trieu .......................... 623/17.16 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2004/0006311 | A1 * | 1/2004 | Shchervinsky .......... 604/164.01 |
| 2004/0176745 | A1 * | 9/2004 | Ferguson ...................... 604/543 |
| 2005/0209574 | A1 * | 9/2005 | Boehringer et al. .......... 604/289 |
| 2005/0240147 | A1 * | 10/2005 | Makower et al. .......... 604/96.01 |
| 2007/0123816 | A1 * | 5/2007 | Zhu et al. ........................ 604/57 |
| 2007/0225738 | A1 | 9/2007 | Pal |
| 2008/0167593 | A1 * | 7/2008 | Fleischmann .................... 602/48 |
| 2008/0188819 | A1 * | 8/2008 | Kloke et al. .................... 604/304 |
| 2008/0281350 | A1 * | 11/2008 | Sepetka et al. ................ 606/200 |
| 2010/0036334 | A1 * | 2/2010 | Heagle et al. ................ 604/319 |
| 2010/0198171 | A1 * | 8/2010 | Spehalski ...................... 604/319 |
| 2011/0034906 | A1 * | 2/2011 | Malhi .......................... 604/543 |

FOREIGN PATENT DOCUMENTS

| AU | 755496 | | 2/2002 |
|---|---|---|---|
| CA | 2005436 | | 6/1990 |
| DE | 26 40 413 | A1 | 3/1978 |
| DE | 43 06 478 | A1 | 9/1994 |
| DE | 295 04 378 | U1 | 10/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | B1 | 8/2004 |
| GB | 692578 | | 6/1953 |
| GB | 2 195 255 | A | 4/1988 |
| GB | 2 197 789 | A | 6/1988 |
| GB | 2 220 357 | A | 1/1990 |
| GB | 2 235 877 | A | 3/1991 |
| GB | 2 333 965 | A | 8/1999 |
| GB | 2 329 127 | B | 8/2000 |
| JP | 4129536 | | 4/1992 |
| SG | 71559 | | 4/2002 |
| WO | WO 80/02182 | | 10/1980 |
| WO | WO 87/04626 | | 8/1987 |
| WO | WO 90/10424 | | 9/1990 |
| WO | WO 93/09727 | | 5/1993 |
| WO | WO 94/20041 | | 9/1994 |
| WO | WO 96/05873 | | 2/1996 |
| WO | WO 97/18007 | | 5/1997 |
| WO | WO 99/13793 | | 3/1999 |
| WO | WO 2006/005939 | A1 | 1/2006 |
| WO | WO 2007/105217 | A2 | 9/2007 |

OTHER PUBLICATIONS

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96.

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G. Živadinović, V. Đukić, Ž. Maksimović, Đ. Radak, and P. Peška, "Vacuum Therapy in the Treatment of Peripheral Blood Vessels," *Timok Medical Journal* 11 (1986), pp. 161-164.

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

* cited by examiner

CATHETER/FILAMENT STYLE DEVICE AND METHODS FOR TREATMENT OF WOUNDS BENEATH THE SURFACE OF THE SKIN

CROSS-REFERENCE TO RELATED APPLICATIONS

This application claims the benefit of U.S. Provisional Application No. 61/052,867, filed May 13, 2008, which is hereby incorporated by reference.

BACKGROUND OF THE INVENTION

1. Field of the Invention

The present invention relates generally to reduced pressure treatment systems and in particular to a system and method for providing a filament to a tissue site and applying reduced pressure to the tissue site through a filament mass formed by the filament.

2. Description of Related Art

Clinical studies and practice have shown that providing a reduced pressure in proximity to a tissue site augments and accelerates the growth of new tissue at the tissue site. The applications of this phenomenon are numerous, but one particular application of reduced pressure has involved treating wounds. This treatment (frequently referred to in the medical community as "negative pressure wound therapy," "reduced pressure therapy," or "vacuum therapy") provides a number of benefits, including migration of epithelial and subcutaneous tissues, improved blood flow, and micro-deformation of tissue at the wound site. Together these benefits result in increased development of granulation tissue and faster healing times. Typically, reduced pressure is applied to tissue through a porous pad or other manifold device.

SUMMARY

The problems presented by existing reduced pressure systems are solved by the systems and methods of the illustrative embodiments described herein. In one illustrative embodiment, a reduced pressure treatment system includes a filament delivery conduit having a distal end positioned at a subcutaneous tissue site of a patient and a proximal end positioned extracorporeal to the patient. A continuous filament is positioned in the filament delivery conduit such that one end of the continuous filament extends from the proximal end of the filament delivery conduit and another end of the continuous filament extends from the distal end of the filament delivery conduit. The continuous filament forms a filament mass adjacent the tissue site. A reduced pressure delivery conduit is adapted to fluidly communicate with a reduced pressure source and the filaments mass to deliver a reduced pressure to the tissue site through the filament mass.

In another illustrative embodiment, a reduced pressure treatment system is provided and includes a catheter having a distal end adapted to be positioned at a subcutaneous tissue site. A bioabsorbable filament is deliverable to the tissue site through a lumen of the catheter such that a filament mass is formed at the tissue site by the bioabsorbable filament. A reduced pressure delivery conduit is adapted to fluidly communicate with a reduced pressure source and the filaments mass to deliver a reduced pressure to the tissue site through the filament mass.

In still another illustrative embodiment, a reduced pressure treatment system includes a continuous monofilament formed into a filament mass and positioned at a tissue site. The reduced pressure treatment system further includes a reduced pressure source in fluid communication with the filament mass to deliver a reduced pressure to the tissue site.

In yet another illustrative embodiment, a reduced pressure treatment system includes a continuous monofilament forming a filament mass and positioned at a tissue site. The reduced pressure treatment system further includes a reduced pressure delivery conduit in fluid communication with the filament mass and adapted to be fluidly connected to a reduced pressure source to deliver a reduced pressure to the tissue site.

In another illustrative embodiment, a method for promoting new tissue growth at a subcutaneous tissue site of a patient includes positioning a distal end of a catheter adjacent the subcutaneous tissue site. A filament is advanced through a lumen of the catheter to the tissue site to form a filament mass at the tissue site, and a reduced pressure is applied to the filament mass at the tissue site.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of several illustrative embodiments, reference is made to the accompanying drawings that form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure associated with tissue at the tissue site. Although the terms "vacuum" and "negative pressure" may be used to describe the pressure applied to the tissue site, the actual pressure reduction applied to the tissue site may be significantly less than the pressure reduction normally associated with a complete vacuum. Reduced pressure may initially generate fluid flow in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

The systems described herein consist of components that enable delivery of a filament to a tissue site and permit application of reduced pressure to the tissue site through a filament mass formed by the filament. Delivery of the filament and reduced pressure may be accomplished by the use of one or more lumens or conduits. Each lumen may be single or multipurpose. The lumens may be part of simple catheters or other devices that can be advanced to the tissue site either separately or together. The lumens within a particular catheter may be arranged parallel, skewed, or coaxial to one another. The cross-sectional shape of the lumens may be circular or any non-circular shape. Optionally, each lumen may be used for venting or purging purposes, for filament delivery or removal, for lavage or other fluid delivery, or for delivery of suction or reduced pressure. When appropriate (e.g. when exposed to vacuum during therapy), each lumen may include means for sealing against negative pressure such as a septum, plug or cap. Such means may include means to seal around filaments or other structures similar to those known in the hemostatic introducer art.

Figure 1:
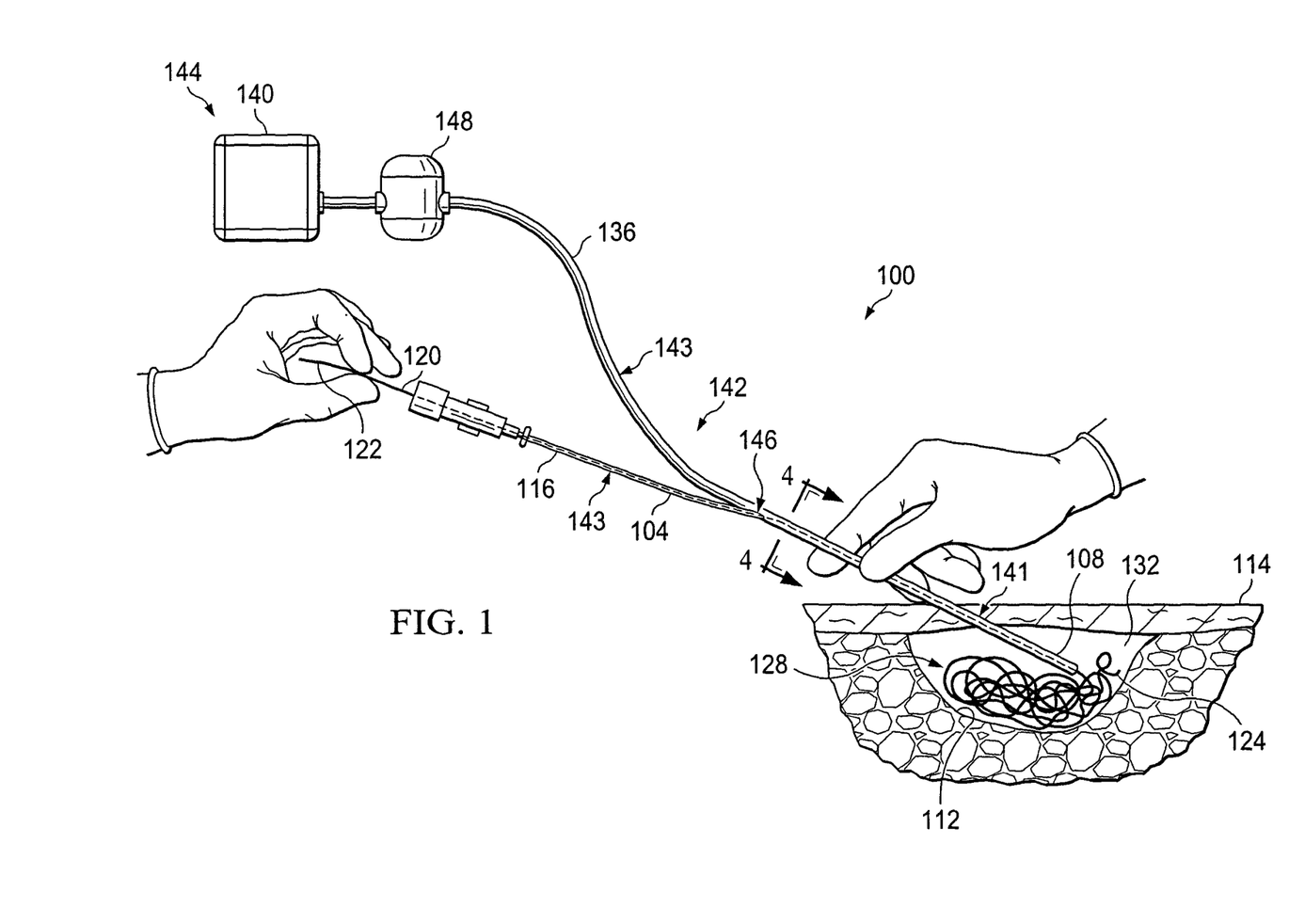
FIG. 1 illustrates a partial cross-sectional side view of a reduced pressure treatment system according to an illustrative embodiment, the reduced pressure treatment system having a catheter for delivering a filament to a tissue site.

Referring to FIGS. 1 and 2, a reduced pressure treatment system 100 according to an illustrative embodiment includes a filament delivery conduit 104 having a distal end 108 adapted to be positioned at a tissue site 112 of a patient 114 and a proximal end 116 that is positioned extracorporeal to the patient. A filament 120, which in the embodiment illustrated in FIG. 1 is a single, continuous, elongated material, is positioned in the filament delivery conduit 104 such that one end 122 of the filament 120 extends from the proximal end 116 of the filament delivery conduit 104 and another end 124 of the filament 120 extends from the distal end 108 of the filament delivery conduit 104. In another embodiment, the filament 120 may be discontinuous and include several separate and unconnected filaments that may be delivered to the tissue site 112 through the filament delivery conduit 104. The filament delivery conduit 104 provides a protected and preferably unobstructed pathway for the filament 120 to be delivered to the tissue site 112. At the tissue site 112, the filament 120 forms into a filament mass 128 as the filament 120 is advanced through the filament conduit 104. The filament mass 128 is positioned adjacent the tissue site 112. In one embodiment, the tissue site 112 is subcutaneous and a void 132 is present adjacent the tissue site 112. Preferably, the filament mass 128 is positioned within the void 132.

Figure 4:
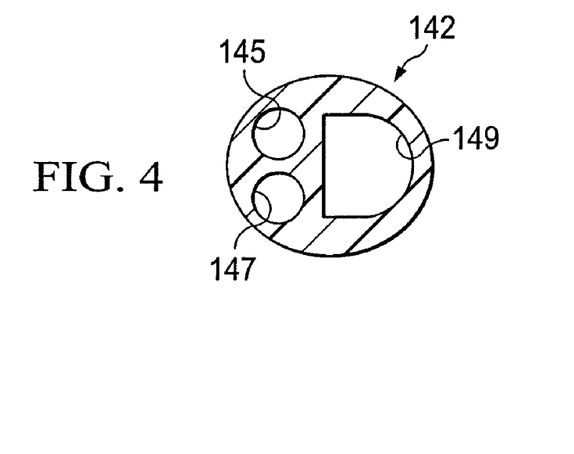
FIG. 4 depicts a cross-sectional view of the catheter of FIG. 1 taken at 4-4.

The reduced pressure treatment system 100 further includes a reduced pressure delivery conduit 136 that is adapted to fluidly communicate with a reduced pressure source 140 and the filament mass 128 such that a reduced pressure is delivered to the tissue site 112 through the filament mass 128. In the embodiment illustrated in FIG. 1, both the reduced pressure delivery conduit 136 and the filament delivery conduit 104 are part of a catheter 142 that may include one or more lumens. In one embodiment, a distal portion 141 of the catheter 142 may include a single lumen that is branched into separate lumens in proximal portions 143 of the catheter 142 at bifurcation 146. Alternatively, separate lumens may be provided in the distal portion 141 of the catheter 142 to keep separate the functions of each lumen. In FIG. 4, a cross-section of the distal portion 141 according to one embodiment illustrates three distinct and separate lumens 145, 147, and 149, two of which are circular in cross-section and another of which is D-shaped in cross-section. Lumen 145 may be used as the filament delivery conduit 104 to deliver the filament 120 to the tissue site 112. Lumen 149 may be used as the reduced pressure delivery conduit 136 to deliver reduced pressure to the tissue site. Lumen 147 may be used either for venting or purging purposes, or for lavage or other fluid delivery.

In one embodiment, separate catheters having separate lumens may be independently or simultaneously delivered to the tissue site to serve as the filament delivery conduit 104 and reduced pressure delivery conduit 136.

The catheters described herein may be constructed from any of a number of materials well known in the art, including without limitation polyethylene, nylon and nylon blends, polyurethane, vinyl, silicone and fluoropolymers. Catheter materials may be any materials with a Shore durometers of 30 A to 75 D. In certain embodiments the catheter(s) will be made from Shore durometers of 80 A to 65 D, and in other embodiments from Shore 55 D to 65 D. Optionally the catheters may be coated with materials well known in the art. In some embodiments the internal lumen may be coated with a hydrogel for reduced friction and/or heparin for reduced thrombogenicity. In some embodiments the exterior may be coated with an antibiotic to reduce the risk of infection.

In the embodiment illustrated in FIG. 1, the reduced pressure source 140 is an electrically-driven vacuum pump. In another implementation, the reduced pressure source 140 may instead be a manually-actuated or manually-charged pump that does not require electrical power, or any other type of reduced pressure pump. In still another embodiment, the reduced pressure source 140 may be a wall suction port such as are available in hospitals and other medical facilities. The reduced pressure source 140 may be housed within or used in conjunction with a reduced pressure treatment unit 144, which may also contain sensors, processing units, alarm indicators, memory, databases, software, display units, and user interfaces that further facilitate the application of reduced pressure treatment to the tissue site 112. In one example, a sensor or switch (not shown) may be disposed at or near the reduced pressure source 140 to determine a source pressure generated by the reduced pressure source 140. The sensor may communicate with a processing unit that monitors and controls the reduced pressure that is delivered by the reduced pressure source 140.

Delivery of reduced pressure to the filament mass 128 and tissue site 112 encourages new tissue growth by maintaining drainage of exudate from the tissue site, increasing blood flow to tissues surrounding the tissue site, and creating microstrain at the tissue site. A canister 148 may be fluidly connected between the reduced pressure source 140 and the tissue site 112 to collect exudate and other fluids drawn from the tissue site 112 and void 132 by the reduced pressure source 140.

In one embodiment, the filament 120 may be constructed from bioresorbable materials that do not have to be removed from a patient's body following reduced pressure treatment. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The filament 120 and filament mass 128 may further serve as a scaffold for new cell-growth, or a scaffold material may be used in conjunction with the filament 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In other embodiments, the filament 120 may be constructed from a non-bioresorbable material. This material may be a monofilament, woven or braided. Suitable material may include, without limitation, polypropylene, polyester, fluoropolymers, polyurethanes and nylons.

The filament mass 128 of the reduced pressure treatment system 100 is a folded or tangled mass formed as the filament 120 is placed at the tissue site 112. While the filament 120 could be placed within the void 132 in an orderly fashion causing the filament 120 to fold in a predictable manner, in most instances it is desirable to allow the filament 120 to randomly kink and fold as it is placed within the void 132. The filament mass 128 may be any size, shape, or thickness, but when used to treat a subcutaneous tissue site, the boundaries of the filament mass 128 are likely defined by the void 132.

The filament mass 128 is adapted to contact the tissue site 112. The filament mass 128 may be partially or fully in contact with the tissue site 112 being treated. When the tissue site 112 is a wound, the filament mass 128 may partially or fully fill the wound. The filament mass 128 acts as a distribution manifold, allowing reduced pressure to be distributed to the tissue site 112 through voids and other spaces that exist within the filament mass 128. These voids and spaces are present in the filament mass 128 due to the loosely-packed nature of the filament 120 in the filament mass 128. When the filament 120 is more tightly-packed, and thus has a greater "density" within the filament mass 128, the volume of voids and spaces within the filament mass 128 is typically less. The volume of the voids and spaces can be increased or decreased depending on a particular tissue site and the amount of reduced pressure that is desired.

The "density" of the filament mass will also affect the ability of the filament 120 to resist collapse of the void 132 when reduced pressure is applied. Since the void 132 is substantially sealed when reduced pressure is applied, the tissue surrounding the void 132 will typically approximate, resulting in a contraction of the void 132. While some contraction is acceptable, the filament mass 128 may aid in preventing complete collapse of the void 132, which allows continued distribution of reduced pressure to the tissue site 112. When the filament mass 128 has a higher density, the filament mass 128 is better able to resist collapse of the void 132.

The filament mass 128 also assists in promoting tissue growth at the tissue site 112 by inducing microstrain at the tissue site 112. As reduced pressure is applied, the tissue site 112 and filament mass 128 are pulled into closer contact with one another, which generates microstrain at the cellular level of the tissue site 112 as the tissue contacts the filaments 120 of the filament mass 128. It is believed that the kinks, twists, and folds of the filament 120 in the filament mass 128 create corners and edges that better enable the filament mass to create microstrain at the tissue site 112.

If the filament mass 128 is positioned adjacent a tissue site that is an open, non-subcutaneous wound, a cover (not shown), or drape, may be positioned over the filament mass 128 and tissue site to maintain reduced pressure beneath the cover at the tissue site. The cover may extend beyond a perimeter of the tissue site and may include an adhesive or bonding agent on the cover to secure the cover to tissue adjacent the tissue site. Alternatively, a sealing layer such as a hydrogel material may be positioned between the cover and the tissue to improve sealing of the cover at the tissue site.

When the filament mass 128 is positioned at a subcutaneous tissue site such as tissue site 112 of FIG. 1, the use of a cover to seal the void 132 to maintain reduced pressure at the tissue site 112 may not be necessary since the void 132 is substantially sealed from ambient by the presence of the patient's own tissue around the void 132. It may be desired, however, to seal around the catheter 142 where the catheter enters the patient. Such sealing may be accomplished by positioning a drape or cover around the catheter 142 where the catheter 142 enters the patient's skin. Alternatively, a suture or adhesive may be placed in this location to better seal around the catheter 142.

Figure 2A:
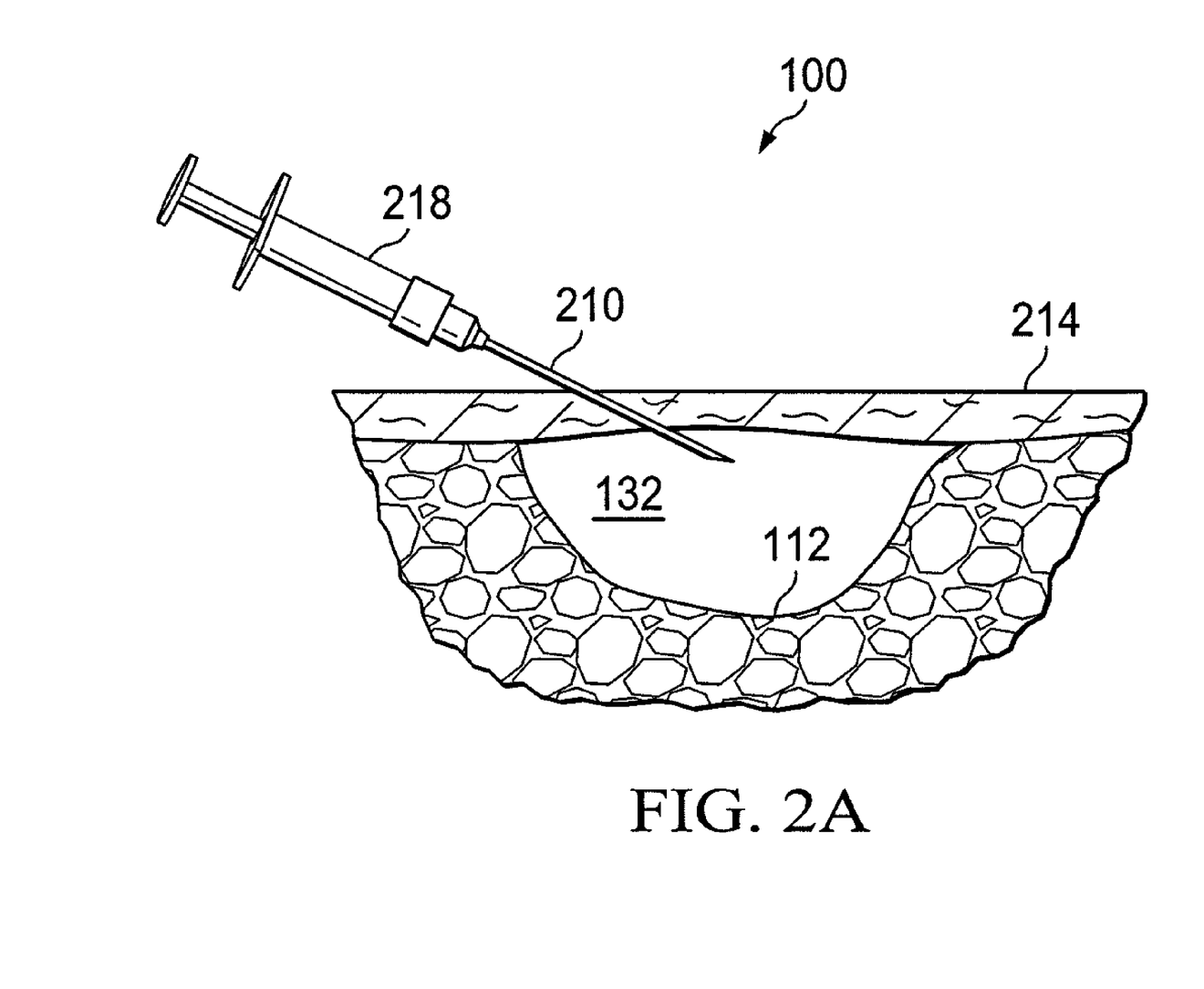
FIGS. 2A-2D depict partial cross-sectional side views of a needle, guide wire, dilator, and sheath to assist in delivering the catheter of FIG. 1 to the tissue site.

Referring to FIGS. 2A-2D, the reduced pressure treatment system 100 may include additional components to assist in guiding and delivering the filament 120 to the tissue site 112. In FIG. 2A, a needle 210 is inserted through skin 214 of the patient and guided to the void 132 adjacent the tissue site 112. The void 132 may be located in or surrounded by any type of tissue beneath the skin 214, thus, it may be required to guide the needle 210 through several layers or types of tissue. The advancement of the needle 210 to the void 132 may be monitored or guided by ultrasound, x-ray, fluoroscopic guidance, or other monitoring or guidance techniques. While the needle 210 of FIG. 2A is illustrated with a syringe 218 attached, the presence of the syringe 218 is optional. If a syringe 218 is attached to the needle 201, the syringe 218 is preferably removed from the needle 210 after insertion to allow direct access to a lumen that passes through the needle 210.

Figure 2B:
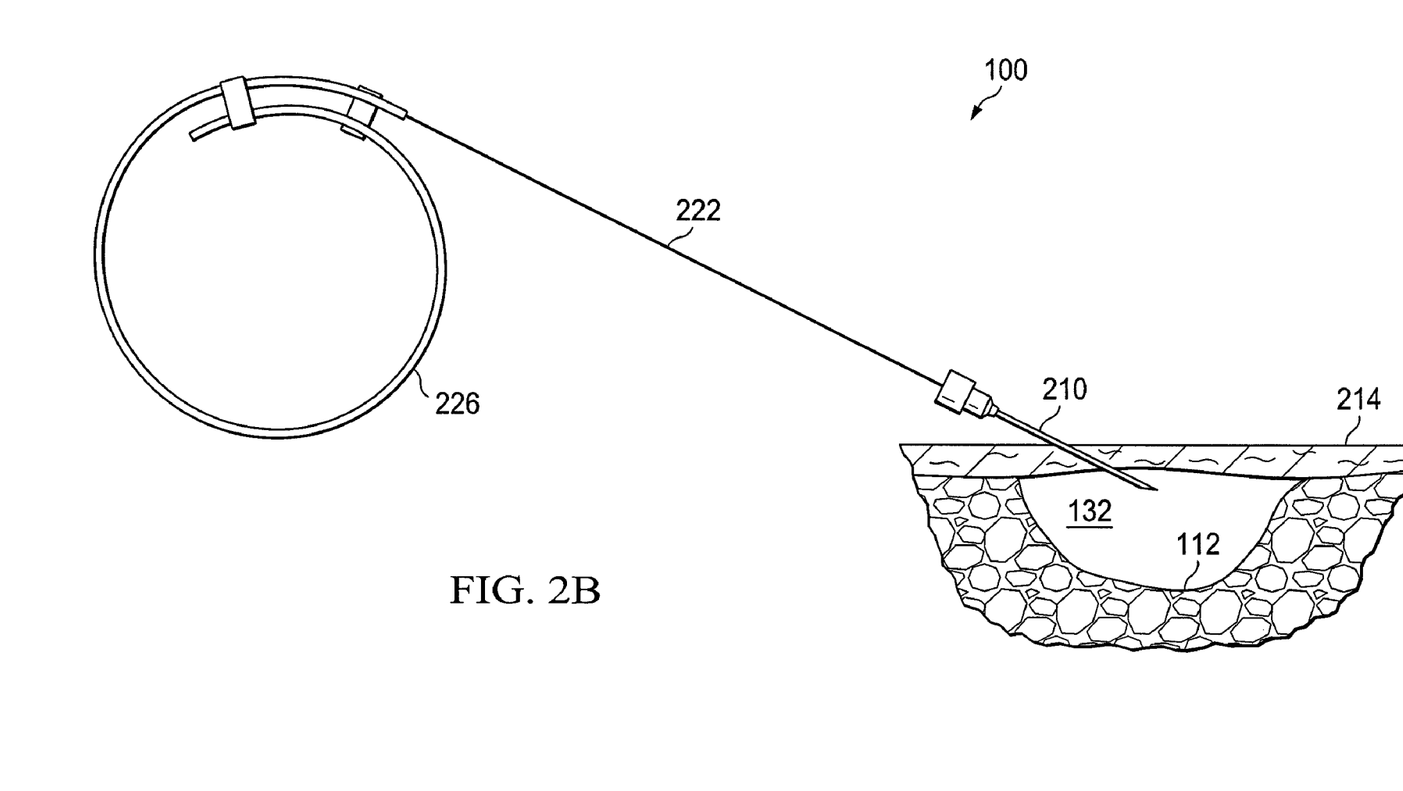

Referring more specifically to FIG. 2B, a guide wire 222 is advanced through the lumen of the needle 210 to the void 132. In one embodiment, the guide wire 222 includes a common configuration of a core covered by a coil to provide additional flexibility. Alternatively, the guide wire 222 may include a less flexible configuration, such as with a stylet or mandrel. The guide wire 222 may be inserted into the lumen by a wire storage device 226. Like the needle 210, the guide wire may be monitored or guided by x-ray, fluoroscopic guidance, or other monitoring or guidance techniques. After delivering an end of the guide wire 222 to the void 132, the needle 210 may be withdrawn from the void 132 and removed from the guide wire 222.

The stylet or mandrel style of guide wire 222 may optionally be made of material of sufficient strength for the wire 222 to be pushed into and through tissues of the body. In one embodiment, the interior diameter of the lumen of the needle 210 and the diameter of the guide wire 222 are sized such that the guide wire 222 can be advanced through the needle 210 without any undue pressure caused by friction. In another embodiment the guide wire can have sufficient stiffness to not require use of a needle. In this case the distal tip of the guide wire includes a sharp trocar or other style tip.

Figure 2C:
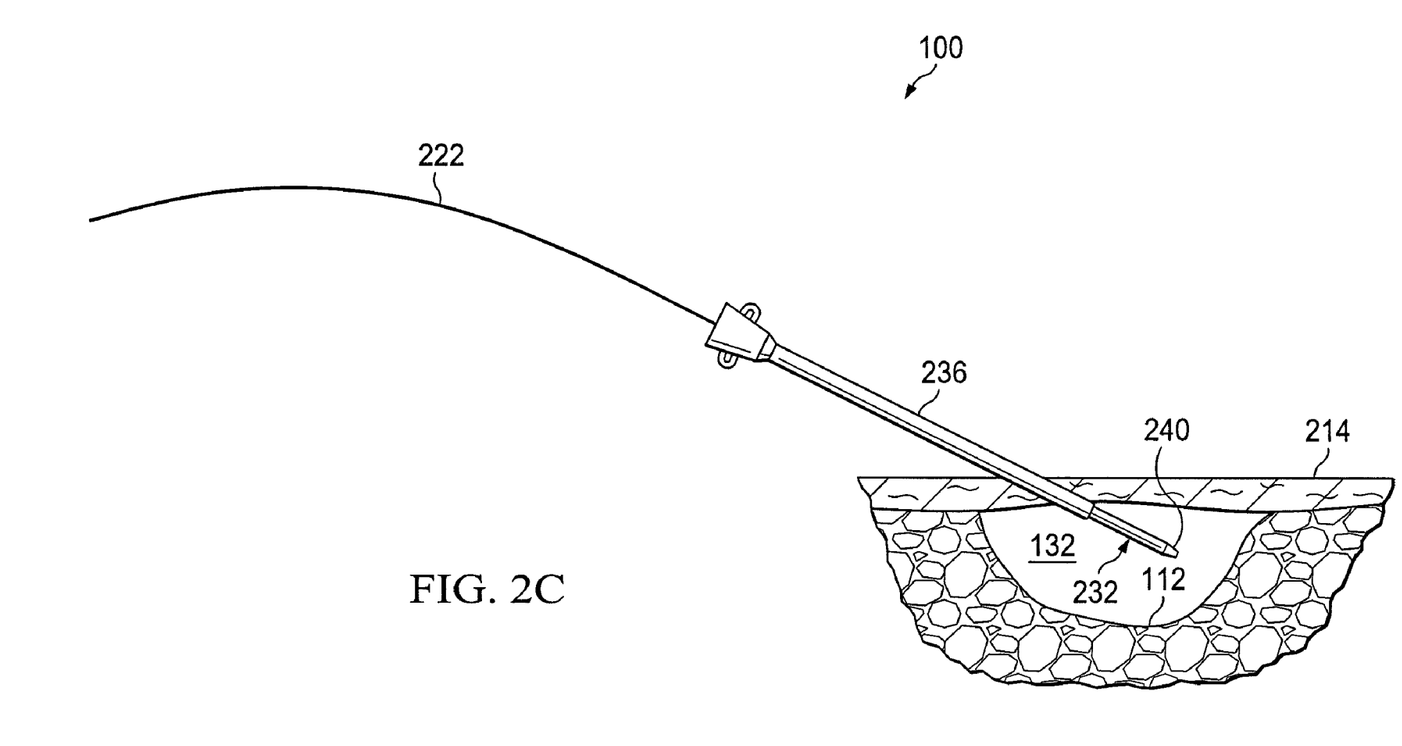

Referring to FIG. 2C, a dilator 232 and a sheath 236 may be advanced along the guide wire 222 to the void 132. While illustrated together, the dilator 232 could be used separately to assist in dilating or dissecting tissue along the guide wire 222 to allow insertion of the sheath 236, or in another embodiment, direct insertion of the catheter 142. The dilator 232 preferably includes a tapered tip 240 to assist in dilating tissue. In the embodiment shown in FIG. 2C, the sheath 236 is positioned coaxially over the dilator 232 and is advanced to the tissue site 112 simultaneously with the dilator 232. In one embodiment, the wall thickness of the sheath 236 is relatively thin to prevent unnecessary dilation or damage to tissue as the dilator 232 and sheath 236 are inserted. The wall thickness of the sheath 236 may in one embodiment be 0.020 inches or less. Following advancement of the sheath 236 to the void 132, the dilator 232 may be removed by withdrawing the dilator 232 along with the guide wire 222 from the patient.

Figure 2D:
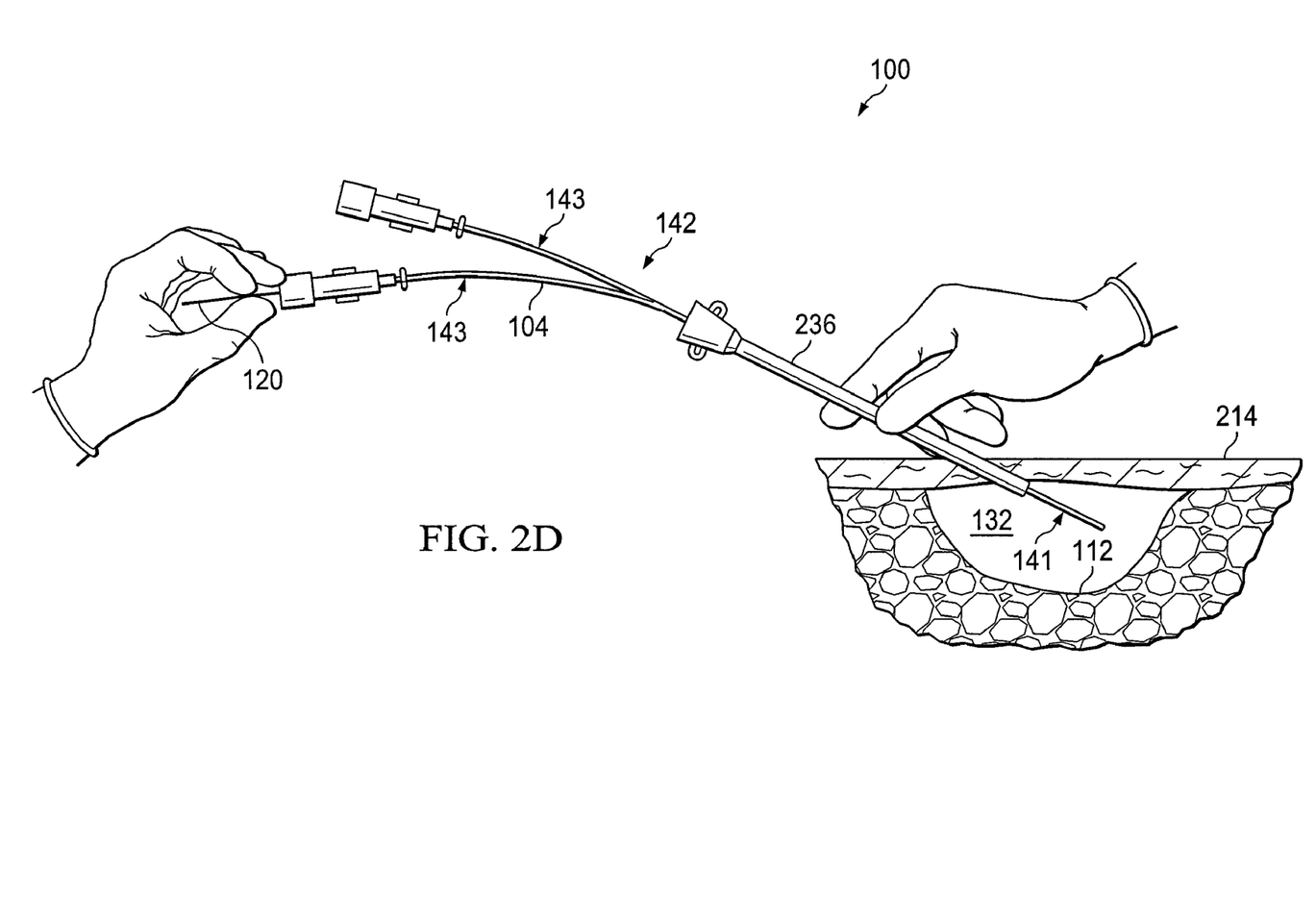

Referring more specifically to FIG. 2D, the catheter 142 may be introduced to the void 132 by advancing the catheter 142 through a lumen of the sheath 236. After the distal portion 141 of the catheter 142 has been delivered to the void 132, the sheath 236 may be removed. In one embodiment, the sheath 236 is a peel or tear-away sheath that is capable of being split or torn apart from the catheter 142 after the sheath 236 is withdrawn from the patient. By having a tear-away configuration, a medical professional is able to more easily remove the sheath 236 from around the catheter 142. In other embodiments the sheath may be left in place to create an annular lumen between the sheath and catheter, to facilitate catheter exchange and/or to serve as a vacuum transmitting lumen after withdrawal of the filament delivery catheter.

Following placement of the catheter 142 at the tissue site 112, the filament 120 is capable of being delivered to the tissue site 112 through a lumen of the catheter 142 such as the filament delivery conduit 104. Multiple systems and methods are capable of delivering the filament 120 to the tissue site 112. Referring to FIGS. 3A-3D, in one embodiment, the reduced pressure treatment system 100 may include a filament feeding system 312. The filament feeding system 312 includes a first tube 316 and a second tube 320. Both the first tube 316 and the second tube 320 include passages through which the filament 120 may be advanced. The first tube 316 includes an outer diameter that is slightly less than an inner diameter of the second tube 320. The relative diameters of the tubes 316, 320 allow the first tube 316 to be telescopically received by the passage of the second tube 320. A gripper member 324 having a passage 328 is operably associated with the second tube 320 and is capable of being moved between an open position illustrated in FIG. 3A and a closed, or gripping, position illustrated in FIG. 3B. In the open position, the size of the passage 328 is such that the filament 120 is permitted to freely pass through the passage 328. In the closed position, the size of the passage 328 is such that the gripper member 324 grips the filament 120 and prevents free movement of the filament 120 through the passage 328. As discussed below, diameters of lumens are selected to balance frictional resistance to advancement of a kinked fiber with the need to keep the fiber aligned with the axis of the lumen and avoid the fiber folding over within the lumen.

Figure 3A:
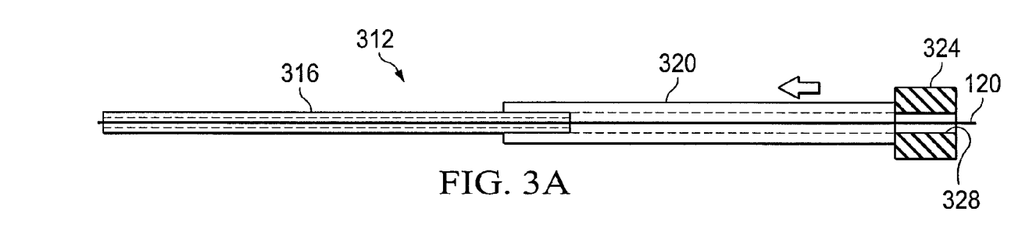
FIGS. 3A-3D illustrate partial cross-sectional side views of a filament feeding system according to an illustrative embodiment, the filament feeding system being used to deliver the filament of FIG. 1 through the catheter to the tissue site.
Figure 3B:
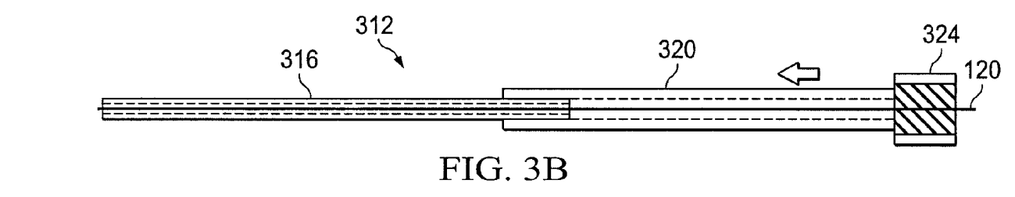
Figure 3C:
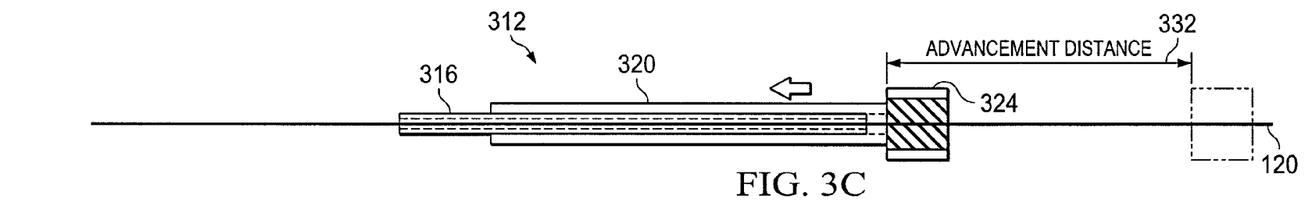
Figure 3D:
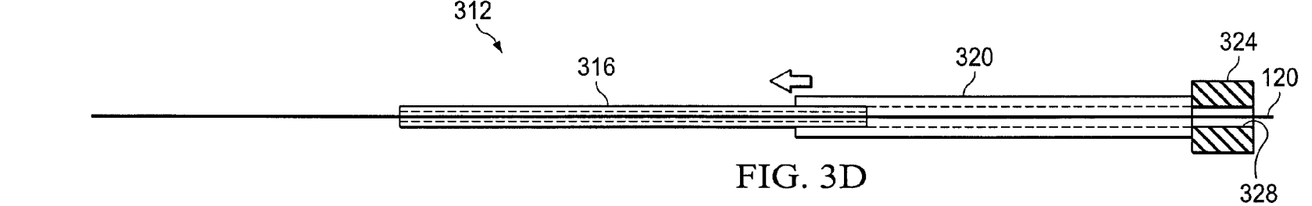

In operation, the filament feeding system 312 is arranged such that one end of the first tube 316 is placed within the passage of the second tube 320. The filament 120 is fed though the gripper passage 328 and through both the first tube 316 and the second tube 320 (see FIG. 3A). The gripper member 324 is then moved to the closed position to grip the filament 120 (see FIG. 3B). The second tube 320 is advanced along the first tube 316 by an advancement distance 332. As the second tube 320 advances, the filament 120 also advances through the first tube 316 by the advancement distance 332. Preferably, the inner diameter of the first tube 316 and second tube 320 is small enough and the stiffness of the filament 120 is great enough that the filament 120 is prevented from binding within the passages of the first and second tubes 316, 320. After moving the second tube 320 onto the first tube 316 as illustrated in FIG. 3C, the gripper member 324 is allowed to return to the open position, and the second tube 320 is retracted from the first tube 316 as illustrated in FIG. 3D. As the second tube 320 is retracted, the filament 120 remains stationary relative to the first tube 316. The movement of the second tube 320, gripper member 324, and filament 120 as shown in FIGS. 3A-3D is repeated to continue the advancement of the filament 120.

In one embodiment, the first tube 316 is a conduit separate from the catheter 142 that may be placed within the filament delivery conduit 104 or the catheter 104 to assist in advancing the filament 120 to the tissue site 112. In another embodiment, the first tube 316 may be the catheter 142 with the passage or lumen of the catheter 142 being the filament delivery conduit 104.

While the filament feeding system 312 provides a quick and effective means of delivering the filament 120 to the tissue site 112, the filament 120 may be delivered to the tissue site 112 by any means convenient to the medical professional. In one embodiment, the filament 120 may be hand-fed or manually advanced through the filament delivery conduit 104. In another embodiment, a reel may be attached to the proximal portion 143 of the catheter 142 to quickly dispense and deliver the filament 120 to the tissue site 112.

In yet another alternate embodiment, the catheter 142 includes means for cutting the filament 120 after the filament 120 has been deployed at the tissue site 112. Such means may include, for example, cutting edges or sharp edges located with the catheter 142.

Figure 5A:
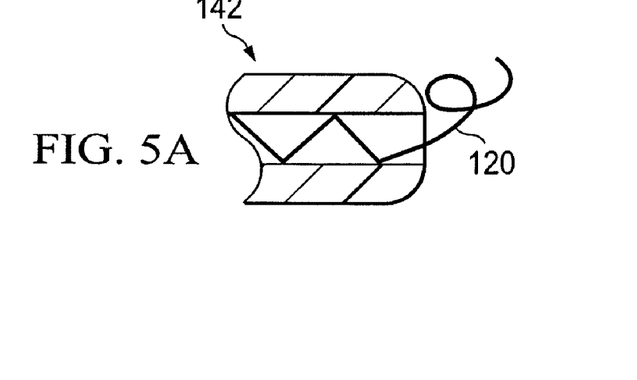
FIGS. 5A and 5B illustrate cross-sectional views of the catheter of FIG. 1 and embodiments showing how the filament may be pre-kinked or positioned prior to advancement through the catheter.
Figure 5B:
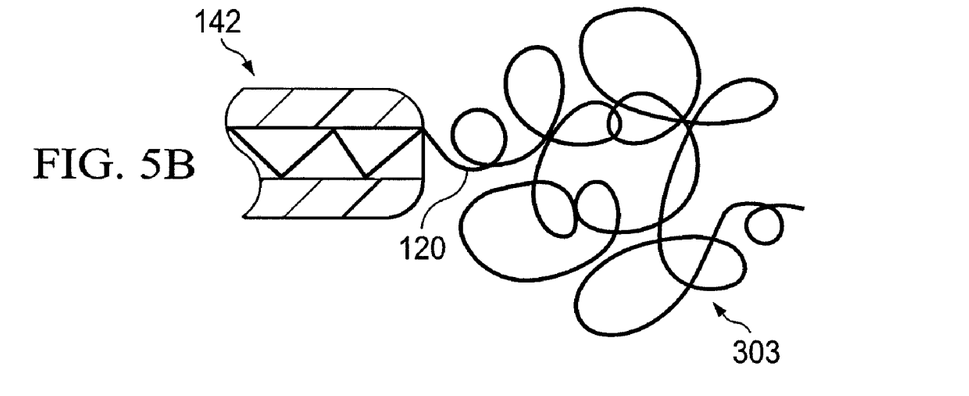

Referring to FIGS. 5A and 5B, in one embodiment, the filament 120 may be advanced to the tissue site 112 as a single, continuous filament. In another embodiment, the filament 120 may include multiple, individual filaments that may be advanced separately or simultaneously to the tissue site 112. The filament 120 may be pre-kinked before being advanced through the catheter 142 to facilitate the filament "balling" or "tangling" to form the filament mass 128. Kinking may optionally include regular (repeating) or irregular (variable) patterns of kink orientation. Kinking may optionally be in a single plane or multi-planar. Once the filament 120 is pre-kinked, it may be advanced through the lumen of the catheter 142, as illustrated in FIG. 5A. The diameters of the filament lumen is selected to balance frictional resistance to advancement of a kinked fiber with the need to keep the fiber aligned with the axis of the lumen and avoid the fiber folding over within the lumen. This is generally accomplished by maintaining lumen diameter to keep the angle between the filament and lumen wall at less than 45 degrees. A non-kinked filament will align substantially parallel with the lumen wall (effectively a 0 degree angle). As the filament 120 is released from the catheter 142, the filament 120 relaxes to begin forming loops, zigzags, waves, crinkles, corkscrews, or other random shapes and positions as illustrated in FIG. 5B. Further, as the distal end of the filament 120 releases from the catheter 142, it may assume or be formed into a pigtail tip to avoid puncture of the tissue site walls, as illustrated in FIG. 5A. As the filament 120 continues to advance into the void 132 adjacent the tissue site 112, the kinks and turns in the filament 120 facilitate the formation of the filament mass 128 by balling or tangling, to fill the void 132 as illustrated in FIG. 5B.

Figure 6:
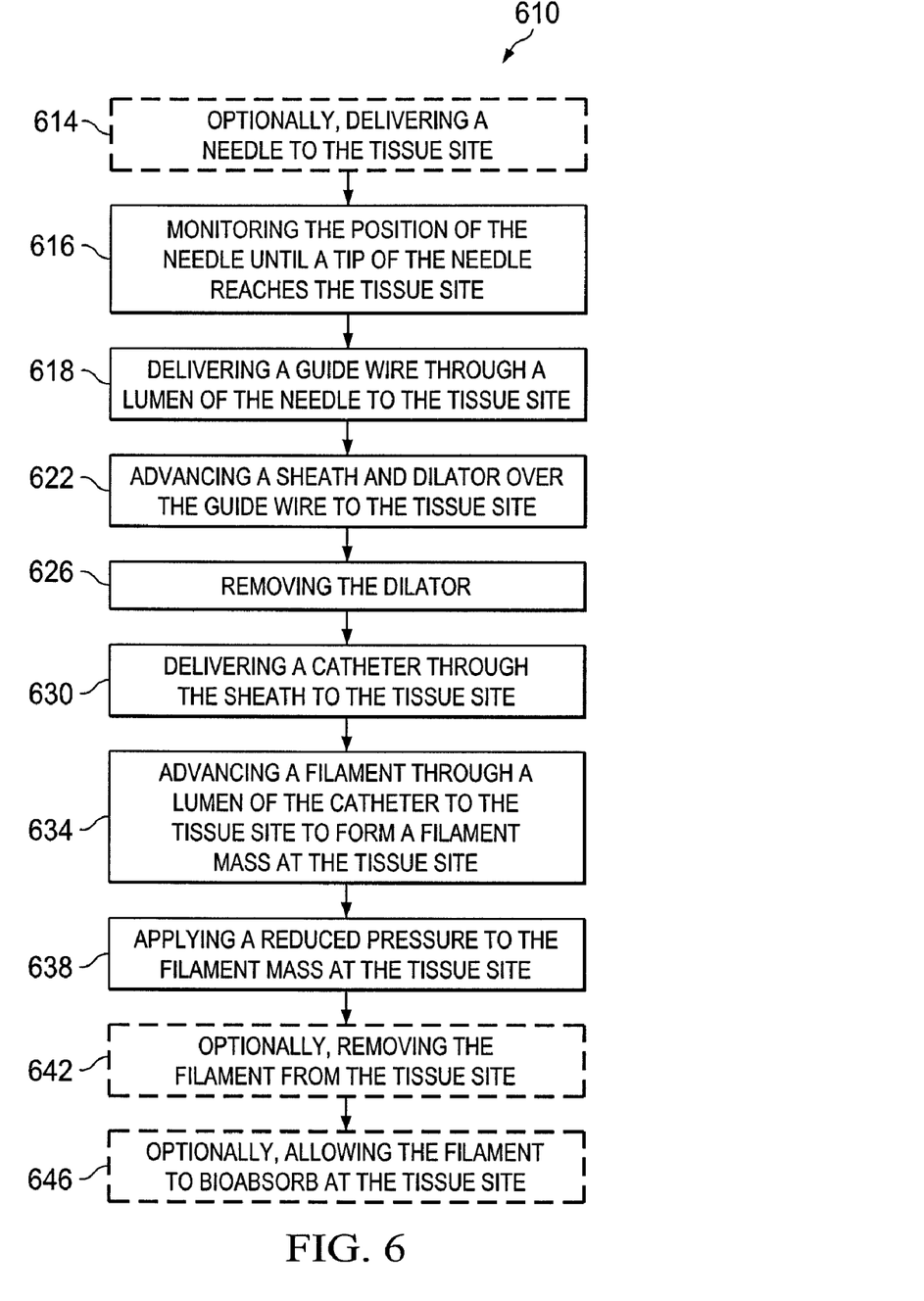
FIG. 6 depicts a method of promoting new tissue growth at a tissue site according to an illustrative embodiment.

Referring to FIG. 6, a method 610 for promoting new tissue growth at a subcutaneous tissue site of a patient optionally includes delivering a needle to the tissue site at 614. At 616, as the needle is delivered, the position of the needle is monitored until a tip of the needle reaches the tissue site. A guide wire is delivered through a lumen of the needle to the tissue site at 618. If a needle is not used prior to insertion of the guide wire, a relatively stiff, pointed guide wire may be advanced directly to the tissue site. The placement and guidance of the guide wire may be monitored by the means described previously for monitoring the placement of the needle. A sheath and dilator are advanced over the guide wire to the tissue site at 622. At 626, the dilator is removed, and a catheter is delivered through the sheath to the tissue site at 630. When the catheter is positioned at the tissue site, a filament may be advanced, as illustrated at 634, through a lumen of the catheter to the tissue site to form a filament mass at the tissue site. At 638, a reduced pressure is applied to the filament mass at the tissue site. Optionally, following reduced pressure treatment, the filament may be removed from the tissue site, as illustrated at 642, or may be left at the tissue site to bioabsorb as illustrated at 646.

It should be apparent from the foregoing that an invention having significant advantages has been provided. While the invention is shown in only a few of its forms, it is not just limited but is susceptible to various changes and modifications without departing from the spirit thereof.

I claim:

1. A reduced pressure treatment system comprising:
   a filament delivery conduit having a distal end positioned at a subcutaneous tissue site of a patient and a proximal end positioned extracorporeal to the patient;
   a continuous filament positioned in the filament delivery conduit such that one end of the continuous filament extends from the proximal end of the filament delivery conduit and another end of the continuous filament extends from the distal end of the filament delivery conduit, the continuous filament forming a filament mass adjacent the subcutaneous tissue site; and
   a reduced pressure delivery conduit adapted to fluidly communicate with a reduced pressure source and the filament mass, the reduced pressure delivery conduit positioned percutaneously to deliver a reduced pressure to the subcutaneous tissue site through the filament mass.

2. The reduced pressure treatment system of claim 1 further comprising:
   a guide wire having an end positionable at the subcutaneous tissue site;
   wherein the filament delivery conduit is a lumen of a catheter; and
   wherein the catheter is advanced to the subcutaneous tissue site over the guide wire.

3. The reduced pressure treatment system of claim 1 further comprising:
   a guide wire having an end positionable at the subcutaneous tissue site;
   a sheath and dilator capable of being advanced over the guide wire to the subcutaneous tissue site;
   wherein the filament delivery conduit is a lumen of a catheter; and
   wherein the catheter is advanced to the subcutaneous tissue site through the sheath following removal of the guide wire and the dilator.

4. The reduced pressure treatment system of claim 3 further comprising:
   a needle capable of being advanced to the subcutaneous tissue site prior to positioning of the guide wire, the guide wire being delivered to the subcutaneous tissue site through a lumen of the needle.

5. The reduced pressure treatment system of claim 1, wherein the reduced pressure delivery conduit is the filament delivery conduit.

6. The reduced pressure treatment system of claim 1, wherein the filament delivery conduit is a first lumen of a catheter and the reduced pressure delivery conduit is a second lumen of the catheter.

7. The reduced pressure treatment system of claim 1, wherein filament delivery conduit and the reduced pressure delivery conduit are separate catheters.

8. The reduced pressure treatment system of claim 1, wherein the filament is a monofilament.

9. The reduced pressure treatment system of claim 1, wherein the filament is a plurality of braided fibers.

10. The reduced pressure treatment system of claim 1, wherein the filament mass is positioned in a void adjacent the subcutaneous tissue site.

11. The reduced pressure treatment system of claim 1, wherein the filament is capable of being removed from the subcutaneous tissue site by pulling on the end of the filament extending from the proximal end of the filament delivery conduit.

12. A reduced pressure treatment system comprising:
    a catheter having a distal end adapted to be positioned at a subcutaneous tissue site;
    a bioabsorbable filament positioned in a lumen of the catheter and deliverable to the tissue site through the lumen of the catheter such that a filament mass is formed at the subcutaneous tissue site by the bioabsorbable filament; and
    a reduced pressure delivery conduit adapted to fluidly communicate with a reduced pressure source and the filament mass, the reduced pressure delivery conduit positioned percutaneously to deliver a reduced pressure to the subcutaneous tissue site through the filament mass.

13. The reduced pressure treatment system of claim 12, wherein a durometer of the catheter is between the range of 80 Shore A and 65 Shore D.

14. The reduced pressure treatment system of claim 12, wherein the catheter is reinforced and a durometer of the catheter is between 30 and 70 Shore A.

15. The reduced pressure treatment system of claim 12 further comprising:
    a guide wire having an end positionable at the subcutaneous tissue site; and
    wherein the catheter is advanced to the subcutaneous tissue site over the guide wire.

16. The reduced pressure treatment system of claim 12 further comprising:
    a guide wire having an end positionable at the subcutaneous tissue site;
    a sheath and dilator capable of being advanced over the guide wire to the subcutaneous tissue site; and
    wherein the catheter is advanced to the subcutaneous tissue site through the sheath following removal of the guide wire and the dilator.

17. The reduced pressure treatment system of claim 16 further comprising:
    a needle capable of being advanced to the subcutaneous tissue site prior to positioning of the guide wire, the guide wire being delivered to the subcutaneous tissue site through a lumen of the needle.

18. The reduced pressure treatment system of claim 12, wherein the lumen of the catheter serves as the reduced pressure delivery conduit.

19. The reduced pressure treatment system of claim 12, wherein the reduced pressure delivery conduit is a second lumen of the catheter.

20. The reduced pressure treatment system of claim 12, wherein the reduced pressure delivery conduit is a second catheter capable of being positioned at the tissue site.

21. The reduced pressure treatment system of claim 12, wherein the filament is a monofilament.

22. The reduced pressure treatment system of claim 12, wherein the filament is continuous.

23. The reduced pressure treatment system of claim 12, wherein the filament remains at the subcutaneous tissue site following cessation of reduced pressure treatment.

24. The reduced pressure treatment system of claim 12, wherein the filament mass is positioned in a void adjacent the tissue site.

\* \* \* \* \*